(12) United States Patent
Banet et al.

(10) Patent No.: US 7,238,159 B2
(45) Date of Patent: Jul. 3, 2007

(54) DEVICE, SYSTEM AND METHOD FOR MONITORING VITAL SIGNS

(75) Inventors: Matthew J. Banet, Del Mar, CA (US); Henk Visser, San Diego, CA (US)

(73) Assignee: Triage Wireless, Inc., San Diego, CA (US)

( * ) Notice: Subject to any disclaimer, the term of this patent is extended or adjusted under 35 U.S.C. 154(b) by 28 days.

(21) Appl. No.: 10/711,492

(22) Filed: Sep. 21, 2004

(65) Prior Publication Data

US 2005/0228298 A1    Oct. 13, 2005

Related U.S. Application Data

(63) Continuation-in-part of application No. 10/709,014, filed on Apr. 7, 2004, now Pat. No. 7,179,228.

(51) Int. Cl.
*A61B 5/00* (2006.01)
*A61B 5/02* (2006.01)

(52) U.S. Cl. ............... 600/485; 600/324; 600/500; 600/504

(58) Field of Classification Search ............. None
See application file for complete search history.

(56) References Cited

U.S. PATENT DOCUMENTS

| | | | |
|---|---|---|---|
| 4,320,767 A | | 3/1982 | Villa-Real |
| 4,338,950 A | * | 7/1982 | Barlow et al. ............ 600/500 |
| 4,869,261 A | | 9/1989 | Penaz |
| 5,025,791 A | * | 6/1991 | Niwa ...................... 600/483 |
| 5,140,990 A | * | 8/1992 | Jones et al. ............. 600/480 |
| 5,309,916 A | * | 5/1994 | Hatschek ................. 600/485 |
| 5,368,026 A | * | 11/1994 | Swedlow et al. ........ 600/323 |
| 5,368,039 A | | 11/1994 | Moses |
| 5,551,438 A | | 9/1996 | Moses |
| 5,941,837 A | * | 8/1999 | Amano et al. ........... 600/595 |
| 5,995,857 A | * | 11/1999 | Toomim et al. ......... 600/322 |
| 6,050,940 A | | 4/2000 | Braun |
| 6,176,831 B1 | | 1/2001 | Voss |
| 6,336,900 B1 | | 1/2002 | Alleckson |
| 6,364,842 B1 | | 4/2002 | Amano |
| 6,375,614 B1 | | 4/2002 | Braun |
| 6,398,727 B1 | | 6/2002 | Bui |
| 6,413,223 B1 | | 7/2002 | Yang |
| 6,443,906 B1 | * | 9/2002 | Ting et al. ............... 600/490 |
| 6,475,153 B1 | * | 11/2002 | Khair et al. ............. 600/485 |
| 6,514,211 B1 | | 2/2003 | Baura |
| 6,546,269 B1 | | 4/2003 | Kurnik |
| 6,605,038 B1 | | 8/2003 | Teller |
| 6,609,023 B1 | | 8/2003 | Fischell |
| 6,612,984 B1 | | 9/2003 | Kerr |
| 6,616,613 B1 | * | 9/2003 | Goodman ................. 600/504 |
| 6,629,930 B2 | * | 10/2003 | Palma et al. ............ 600/485 |
| 6,705,990 B1 | * | 3/2004 | Gallant et al. .......... 600/300 |
| 6,893,402 B2 | * | 5/2005 | Freund et al. ........... 600/485 |

\* cited by examiner

*Primary Examiner*—Charles A. Marmor, II
*Assistant Examiner*—Patricia Mallari (57) ABSTRACT

A monitoring device, method and system are disclosed herein. The monitoring device is capable of determine when a user's wrist is at rest using a motion sensor disposed within a wrist module that is attached to the user's wrist. When at rest, the monitoring device utilizes a vital sign monitor to determine a plurality of vital signs of the user. The vital sign monitor preferably comprises a light source and photodetector in communication with a pulse-oximetry circuit. The motion sensor is preferably an accelerometer.

19 Claims, 10 Drawing Sheets

DEVICE, SYSTEM AND METHOD FOR MONITORING VITAL SIGNS

CROSS REFERENCE TO RELATED APPLICATION

This application is a continuation-in-part application of U.S. patent application Ser. No. 10/709,014, filed on Apr. 7, 2004 now U.S. Pat. No. 7,179,228

BACKGROUND OF THE INVENTION

1. Field of the Invention

The present invention relates to devices for monitoring vital signs. More specifically, the present invention relates to devices for monitoring blood pressure.

2. Description of the Related Art

Blood within a patient's body is characterized by a baseline pressure value, called the diastolic pressure. Diastolic pressure indicates a pressure in an artery when the blood it contains is static. A heartbeat forces a time-dependent volume of blood through the artery, causing the baseline pressure to increase in a pulse-like manner to a value called the systolic pressure. The systolic pressure indicates a maximum pressure in a portion of the artery that contains a flowing volume of blood.

Pressure in the artery periodically increases from the diastolic pressure to the systolic pressure in a pulsatile manner, with each pulse corresponding to a single heartbeat. Blood pressure then returns to the diastolic pressure when the flowing pulse of blood passes through the artery.

Both invasive and non-invasive devices can measure a patient's systolic and diastolic blood pressure. A non-invasive medical device called a sphygmomanometer measures a patient's blood pressure using an inflatable cuff and a sensor (e.g., a stethoscope) that detects blood flow by listening for sounds called the Korotkoff sounds. During a measurement, a medical professional typically places the cuff around the patient's arm and inflates it to a pressure that exceeds the systolic blood pressure. The medical professional then incrementally reduces pressure in the cuff while listening for flowing blood with the stethoscope. The pressure value at which blood first begins to flow past the deflating cuff, indicated by a Korotkoff sound, is the systolic pressure. The stethoscope monitors this pressure by detecting strong, periodic acoustic 'beats' or 'taps' indicating that the blood is flowing past the cuff (i.e., the systolic pressure barely exceeds the cuff pressure). The minimum pressure in the cuff that restricts blood flow, as detected by the stethoscope, is the diastolic pressure. The stethoscope monitors this pressure by detecting another Korotkoff sound, in this case a 'leveling off' or disappearance in the acoustic magnitude of the periodic beats, indicating that the cuff no longer restricts blood flow (i.e., the diastolic pressure barely exceeds the cuff pressure).

Low-cost, automated devices measure blood pressure using an inflatable cuff and an automated acoustic or pressure sensor that measures blood flow. These devices typically feature cuffs fitted to measure blood pressure in a patient's wrist, arm or finger. During a measurement, the cuff automatically inflates and then incrementally deflates while the automated sensor monitors blood flow. A microcontroller in the automated device then calculates blood pressure. Cuff-based blood-pressure measurements such as these typically only determine the systolic and diastolic blood pressures; they do not measure dynamic, time-dependent blood pressure.

Time-dependent blood pressure can be measured with a device called a tonometer. The tonometer typically includes a sensitive transducer that contacts a patient's skin and compresses an underlying artery against a portion of bone. The transducer then measures blood pressure in the form of a time-dependent waveform. The waveform features a baseline that indicates the diastolic pressure, and time-dependent pulses, each corresponding to individual heartbeats. The maximum and minimum values of each pulse are, respectively, the systolic and diastolic pressures. The rising and falling edges of each pulse correspond to pressure values that lie between the systolic and diastolic pressures.

Data indicating blood pressure are most accurately measured during a patient's appointment with a medical professional, such as a doctor or a nurse. Once measured, the medical professional manually records these data in either a written or electronic file. Appointments typically take place a few times each year. Unfortunately, in some cases, patients experience 'white coat syndrome' where anxiety during the appointment affects the blood pressure that is measured. White coat syndrome typically elevates a patient's heart rate and blood pressure; this, in turn, can lead to an inaccurate diagnoses.

Blood pressure monitors can also be used in an ambulatory setting to counteract white coat syndrome. In this case, the monitors are worn by patients over a short (e.g., 24-hour) period, and are programmed to make periodic measurements (e.g., once every hour). Some ambulatory blood pressure monitors include systems for transmitting data from a remote site, such as the patient's home, to a central database. These systems can include a conventional computer modem that transmits data through a telephone line to the database. Or alternatively they can include a wireless transmitter, such as a cellular telephone, which wirelessly transmits the data through a wireless network.

Monitoring a patient's blood pressure, particularly in an ambulatory setting, can be difficult since a measurement may be taken when the patient's limb is in motion, thereby skewing the reading. It would therefore be desirable to have a device that indicates when the patient's limb is at rest and at an optimal time to take a blood pressure measurement.

BRIEF SUMMARY OF THE INVENTION

The present invention is able to determine when a patient's limb is in motion or at rest in order to measure the patient's blood pressure using a device that both wireless and cuffless. The present invention allows for accurate measurements at a patient's home, office or elsewhere outside of a conventional medical facility.

One aspect of the present invention is a device for monitoring a patient's blood pressure that makes a cuffless measurement and transmits this information wirelessly to an Internet-based server. The device includes a motion sensor, a vital sign monitor, a microprocessor and a short-range wireless transceiver. The motion sensor monitors the localized motion of the patient. The vital-sign monitor monitors the blood pressure of the patient. The microprocessor receives blood pressure information from the vital sign monitor and motion information from the motion sensor. The microprocessor distinguishes between blood pressure information received during localized motion of the patient and during localized rest of the patient. The short-range wireless transceiver transmits blood pressure information from the microprocessor.

Yet another aspect of the present invention is a method for monitoring a patient's blood pressure. The method begins with determining if the patient's hand is at rest or in motion. Next, a vital sign monitor is activated to generate blood pressure information if the patient's hand is determined to be at rest. Next, the blood pressure information is sent to a microprocessor for processing to generate a blood pressure signal for the patient, Next, the blood pressure signal for the patient is wirelessly transmitted to a computer or handheld device.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
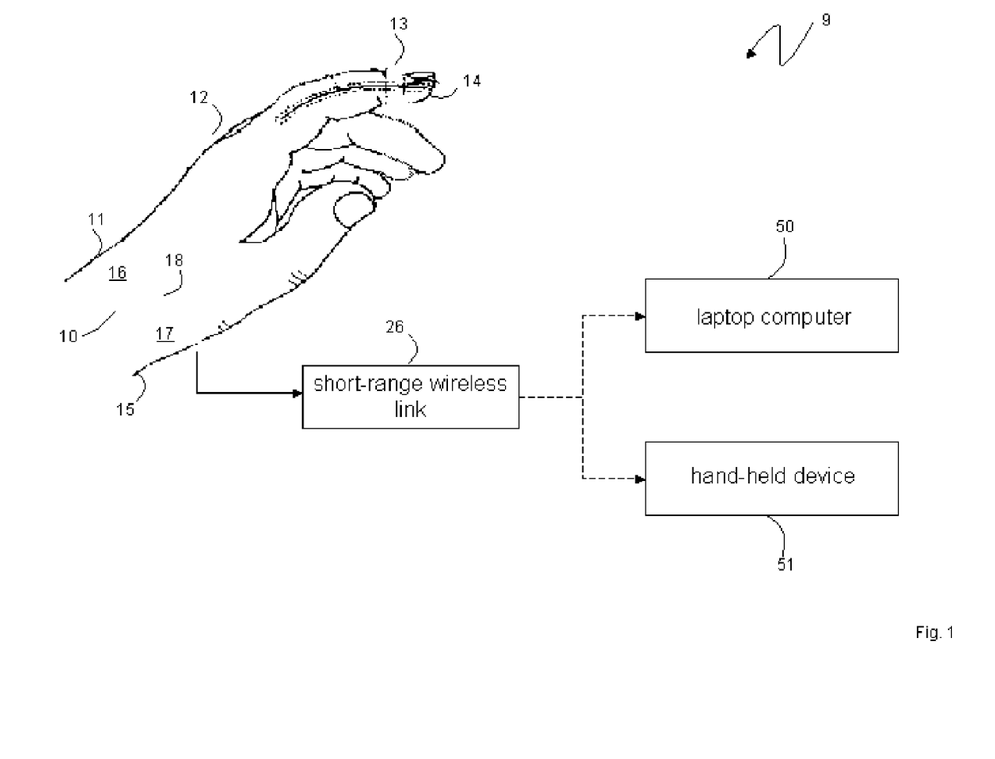
FIG. 1 is a schematic side view of a monitoring system for measuring motion and vital signs according to the present invention.
Figure 2:
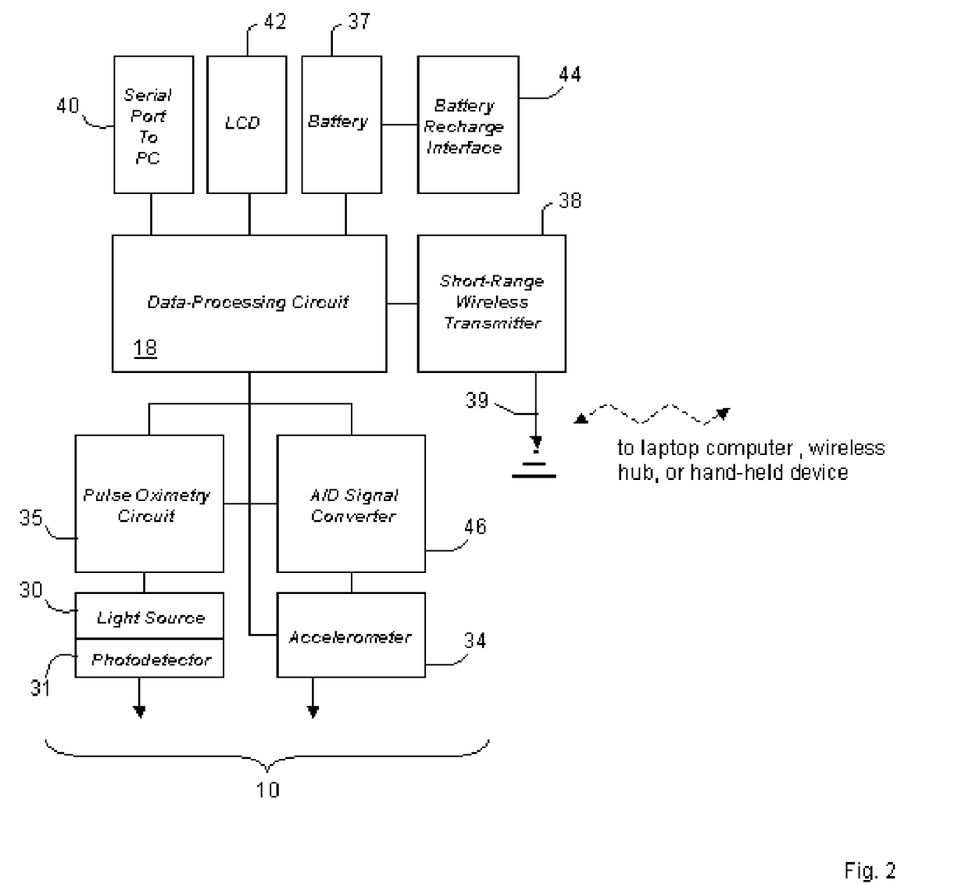
FIG. 2 is a schematic view of circuit components utilized in a monitoring device of the present invention.

FIGS. 1 and 2 show a monitoring system 9 that measures vital signs, motion, and even impact forces from a user's wrist 15. The system 9 features a monitoring device 10 that measures and wirelessly transmits the measurements through a short-range wireless link 26 to an external laptop computer 50 or hand-held device 51 for further processing with a software program stored in a memory, or for transmission over a network such as disclosed in co-pending U.S. patent application Ser. No. 10/810,237, filed Mar. 26, 2004, for a CUFFLESS BLOOD PRESSURE MONITOR AND ACCOMPANYING WEB SERVICES INTERFACE, co-pending U.S. patent application Ser. No. 10/709,015, filed Apr. 7, 2004, CUFFLESS BLOOD-PRESSURE MONITOR AND ACCOMPANYING WIRELESS, INTERNET-BASED SYSTEM, or co-pending U.S. patent application Ser. No. 10/752,198, filed Jan. 6, 2004, for a WIRELESS, INTERNET-BASED MEDICAL DIAGNOSTIC SYSTEM, all of which are hereby incorporated by reference in their entirety. The monitoring device 10 preferably includes a wrist-mounted module 11 that attaches to an area of the user's wrist 15 where a watch is typically worn, and a finger-mounted module 13 that attaches to the user's index finger 14. A cable 12 preferably provides an electrical connection between the finger-mounted module 13 and wrist-mounted module 11.

In a preferred embodiment, the wrist-mounted module 11 preferably comprises a motion sensor 17, a data-processing circuit 18, a short-range wireless transceiver 38, a pulse-oximetry circuit 35, a power source 37 and an antenna 39. The components are preferably embedded within a comfortable, non-conductive material, such as neoprene or silicone rubber. The finger-mounted module 13 preferably comprises a vital sign monitor 16, as discussed in greater detail below.

To measure motion, and even impact forces, the motion sensor 17 is located in the wrist-mounted module 11. A preferred motion sensor 17 is an accelerometer, and the accelerometer is preferably embedded in the wrist-mounted module 11. In typical embodiments, the motion sensor 17 is a multi-axis accelerometer, such as the ADXL202 made by Analog Devices of Norwood, Mass. This device is a standard MEMs (microelectronic machine) module that measures acceleration and deceleration using an array of silicon-based structures. Alternatively, the motion sensor 17 is a mercury switch or piezoelectric device. In other embodiments, the motion sensor is a computer algorithm that analyzes the information from the vital sign monitor (e.g., an optical waveform, described in more detail below) to determine motion-induced abnormalities. For example, a high degree of non-periodic 'noise' in the waveform, or a rapid change in the waveform's, intensity may indicate motion. In general, the computer algorithm can analyze any profound change in the waveform, other than that due to the user's heartbeat, to determine motion.

The motion sensor 17 senses acceleration, deceleration, and general motion, and sends this information to a data-processing circuit 18. Preferably, the motion sensor 17 is used to detect when a user's hand is at rest, and is therefore in an optimal state to measure the user's vital signs with the vital sign monitor 16. In this manner, the motion sensor 17 reduces artifacts related to movement from the vital sign measurement.

The data-processing circuit 18, which features a microprocessor, controls the monitoring device 10. The term 'microprocessor', as used herein, preferably means a silicon-based microprocessor or microcontroller that operates compiled computer code to perform mathematical operations on data stored in a memory. Examples include ARM7 or ARM9 microprocessors manufactured by a number of different companies; AVR 8-bit RISC microcontrollers manufactured by Atmel; PIC CPUs manufactured by Microchip Technology Inc.; and high-end microprocessors manufactured by Intel and AMD.

The short-range wireless transceiver 38 is preferably a transmitter operating on a wireless protocol, e.g. BLUETOOTH®, part-15, ZIGBEE®, or 802.11. "Part-15" refers to a conventional low-power, short-range wireless protocol, such as that used in cordless telephones.The short-range wireless transmitter 38 (e.g., a BLUETOOTH® transmitter) receives information from the data-processing circuit 18 and transmits this information in the form of a packet through an antenna 39. The external laptop computer 50 or hand-held device 51 features a similar antenna coupled to a matched wireless, short-range receiver that receives the packet. In certain embodiments, the hand-held device 51 is a cellular telephone with a BLUETOOTH® circuit integrated directly into a chipset used in the cellular telephone. In this case, the cellular telephone may include a software application that receives, processes, and displays the information. The laptop computer 50 or hand-held device 51 may also include a long-range wireless transmitter that transmits information over a terrestrial, satellite, or 802.11-based wireless network. Suitable networks include those operating at least one of the following protocols: CDMA, GSM, GPRS, Mobitex, DataTac, iDEN, and analogs and derivatives thereof.

The wireless transceiver 38 generally sends information following an 'event', such as when the user's hand comes to rest. The data-processing firmware, operating on the internal, embedded microprocessor 18, detects such an event. The firmware can also process signals from the vital-sign monitor, as is described in more detail below.

In a complementary manner, the vital sign monitor 16 in the finger-mounted module 13 measures information that is processed to determine the user's vital signs. Specifically, the vital sign monitor 16 in the finger-mounted module 13 measures blood flow in the user's finger, and sends this information through the cable 12 to the wrist-mounted module 11. During operation, the vital sign monitor 16 measures an optical 'waveform' that is processed, as described detail below, to determine diastolic and systolic blood pressure, real-time beat-to-beat blood pressure, heart rate, and pulse oximetry. Other vital sign monitors are disclosed in co-pending U.S. patent application Ser. No. 10/709,014, filed Apr. 7, 2004, for a CUFFLESS SYSTEM FOR MEASURING BLOOD PRESSURE, which is hereby incorporated by reference in its entirety.

Additional software programs can further analyze the user's blood pressure, heart rate, and pulse oximetry values to characterize the user's cardiac condition. These programs, for example, may provide a report that features statistical analysis of these data to determine averages, data displayed in a graphical format, trends, and comparisons to doctor-recommended values. The monitoring system 9 measures cardiac, motion, and impact force information non-invasively with basically no inconvenience to the user.

FIG. 2 shows, in detail, electronic components featured in the monitoring device 10. In a preferred embodiment, an accelerometer 34 connects to an analog-to-digital converter 46 within the data-processing circuit 18 to measure motion, acceleration, and deceleration of the user's wrist. Specifically, the analog-to-digital converter 46 samples the variable voltage generated by the accelerometer 34, and in response generates a time-dependent voltage value that the data-processing circuit 18 receives, stores in an internal memory, and then analyzes as described with reference to FIG. 7. A battery 37 powers all the electrical components within the monitoring device 10, and is typically a metal hydride battery (typically generating 5V) that can be recharged through a battery-recharge interface 44. In an alternative embodiment, the monitoring device 10 can include an LCD 42 that displays information for the user or patient. In another embodiment, the data-processing circuit 18 avails calculated information through a serial port 40 to an external personal computer, which then displays and analyzes the information using a client-side software application.

Figure 1A:
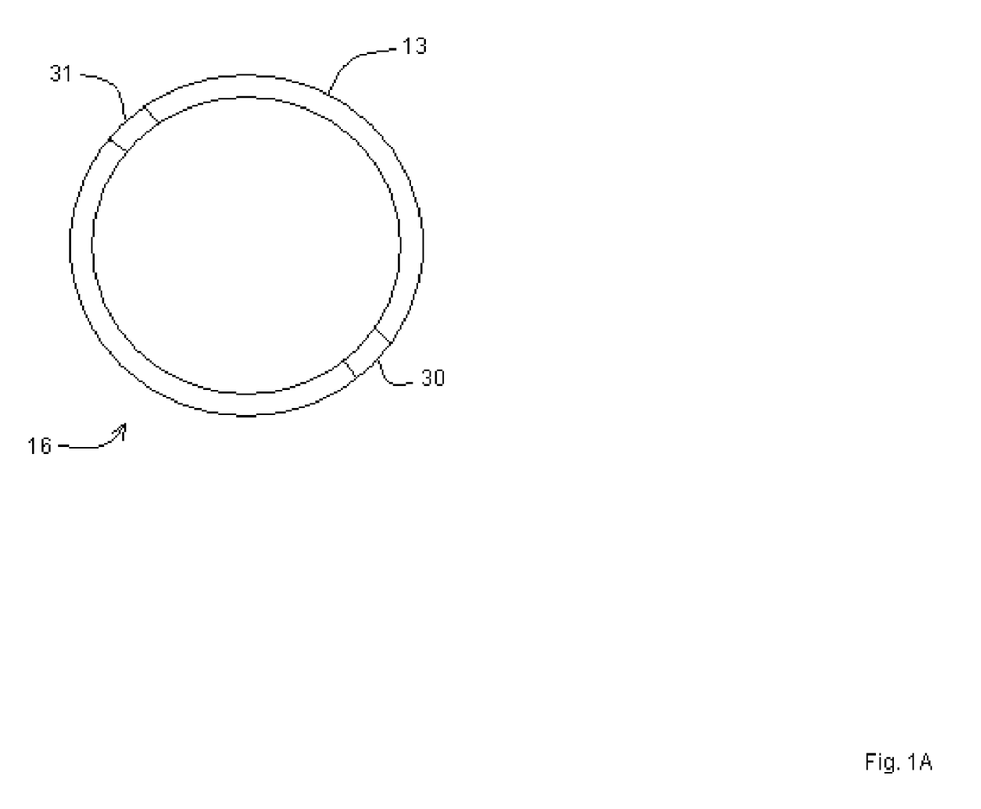
FIG. 1A is an isolated cross-sectional view of a finger-mounted module of the present invention.

To generate an optical waveform and measure blood pressure, pulse oximetry, heart rate, along with various statistics (e.g., average values, standard deviation) of this information, the vital sign monitor 16 connected to the finger-mounted module 13 preferably includes a light source 30 and a photodetector 31 embedded within the finger-mounted module 13, as shown in FIG. 1A. The finger-mounted module 13 is preferably composed of a flexible polymer material. The light source 30 typically includes light-emitting diodes that generate both red (wavelength~630 nm) and infrared (wavelength~900 nm) radiation. As the heart pumps blood through the patient's finger, blood cells absorb and transmit varying amounts of the red and infrared radiation depending on how much oxygen binds to the cells' hemoglobin. The photodetector 31 detects transmission at the red and infrared wavelengths, and in response generates a radiation-induced current that travels through a cable to the pulse-oximetry circuit 35 embedded within the wrist-worn module 11. The pulse-oximetry circuit 35 connects to the analog-to-digital signal converter 46. The analog-to-digital signal converter 46 converts the radiation-induced current into a time-dependent optical waveform, which is then sent back to the pulse-oximetry circuit 35 and data-processing circuit 18 and analyzed to determine the user's vital signs as described in this application and the above-mentioned co-pending patent applications, the contents of which have been incorporated by reference.

Figure 3:
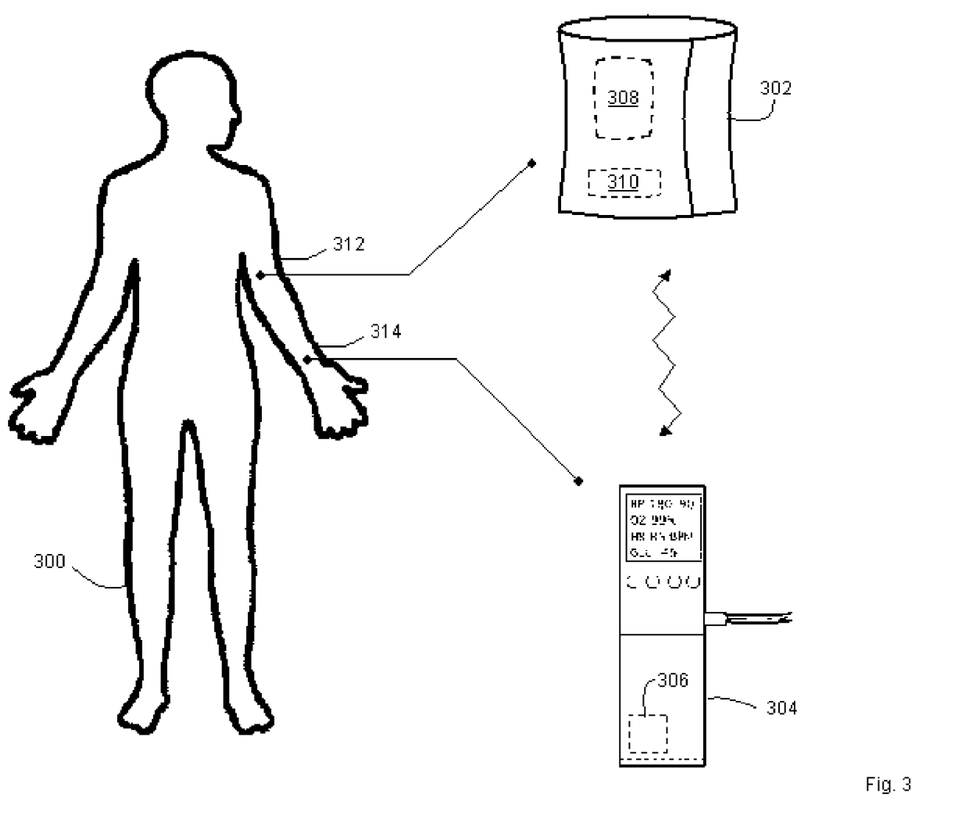
FIG. 3 is a schematic diagram of a calibration system used with the present invention.

FIG. 3 shows schematically how the above-described monitoring device 10 measures blood pressure from a patient 300 using a calibration-based approach. In a preferred embodiment, the monitoring device 10 measures blood pressure using calibration parameters in combination with an optical measurement made as described above. Calibration parameters are determined prior to the measurement using a conventional blood-pressure cuff 302 that temporarily attaches to an upper portion 312 of the patient's arm. Immediately prior to measurement, a short-range radio transmitter 310 embedded in the blood-pressure cuff 302 sends a wireless signal to a matched short-range radio receiver 306 in the monitoring device 10 worn on the patient's wrist 314. The signal indicates that the calibration measurement is about to begin. Once the signal is received, the blood-pressure cuff 302 and monitoring device 10 simultaneously collect, respectively, blood pressure values (systolic, diastolic pressures) and a corresponding optical waveform. The blood pressure cuff 302 measures systolic and diastolic blood pressure using an electronic system 308 that includes a motor-controlled pump and data-processing electronics. Systolic and diastolic blood pressures are the calibration parameters that the short-range radio transmitter sends wirelessly to the monitoring device 10 once the calibration measurement is completed. This process is repeated at a later time (e.g., 15 minutes later) to collect a second set of calibration parameters. The blood-pressure cuff 302 is then removed.

Figure 4:
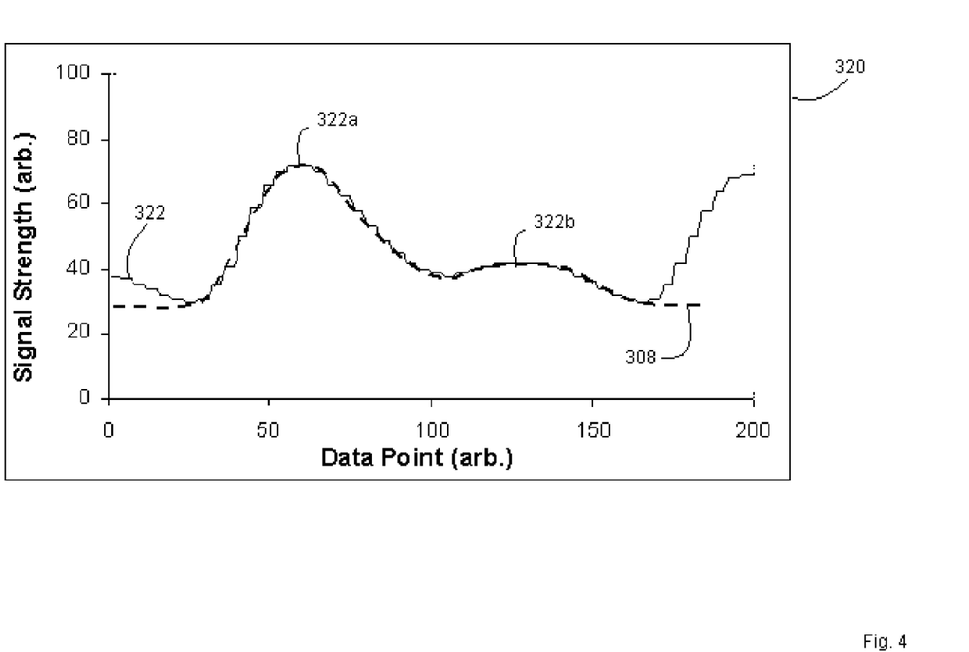
FIG. 4 is a graph of a single pulse from an optical waveform generated from the calibration system.

The first and second calibration parameters, along with their corresponding optical waveforms, are stored in memory in the monitoring device 10 and then analyzed with the data-processing circuit 18 shown in FIG. 2 to complete the calibration. FIG. 4 features a graph 320 that indicates how this analysis is performed on a single pulse 322 from the optical waveform. The pulse 322 varies with time and features a primary peak 322a that represents blood flowing through the patient's arteries with each heartbeat, and a secondary peak 322b that represents a 'reflection' of the primary peak that occurs within the patient's circulatory system. Once collected, the pulse 322 is 'fit' using a numerical function that accurately describes the pulse's features, and an algorithm that iteratively varies the parameters of the function until it best matches the time-dependent features of the pulse 322. The graph 320 includes a dashed line 308 that represents the fit. Since the dashed line 308 is a numerical function, its parameters can be easily stored in memory and analyzed with the data processing circuit to calibrate the monitoring device 10. For example, the data-processing circuit 18 can determine the patient's heart rate by measuring the average time difference between successive pulses. The data-processing circuit 18 can also process relative amplitudes between the secondary 322b and primary 322a peaks to determine a numerical ratio. In other embodiments, the data-processing circuit takes a mathematical derivative (e.g., a first or second derivative) of the pulse 322, and then fits and analyzes this in a manner similar to that described above. Once these properties are determined, they are compared to the systolic and diastolic blood pressure values measured simultaneously by the blood-pressure cuff 302 to generate numerical calibration curves. The calibration curves can be linear or non-linear, and typically vary with each patient. During subsequent measurements, the cuff 302 is removed, and optical waveforms are measured and fit as described above to determine, e.g., heart rate and the numerical ratio. This information is compared to the calibration curves to determine blood pressure without using a cuff.

Figure 5:
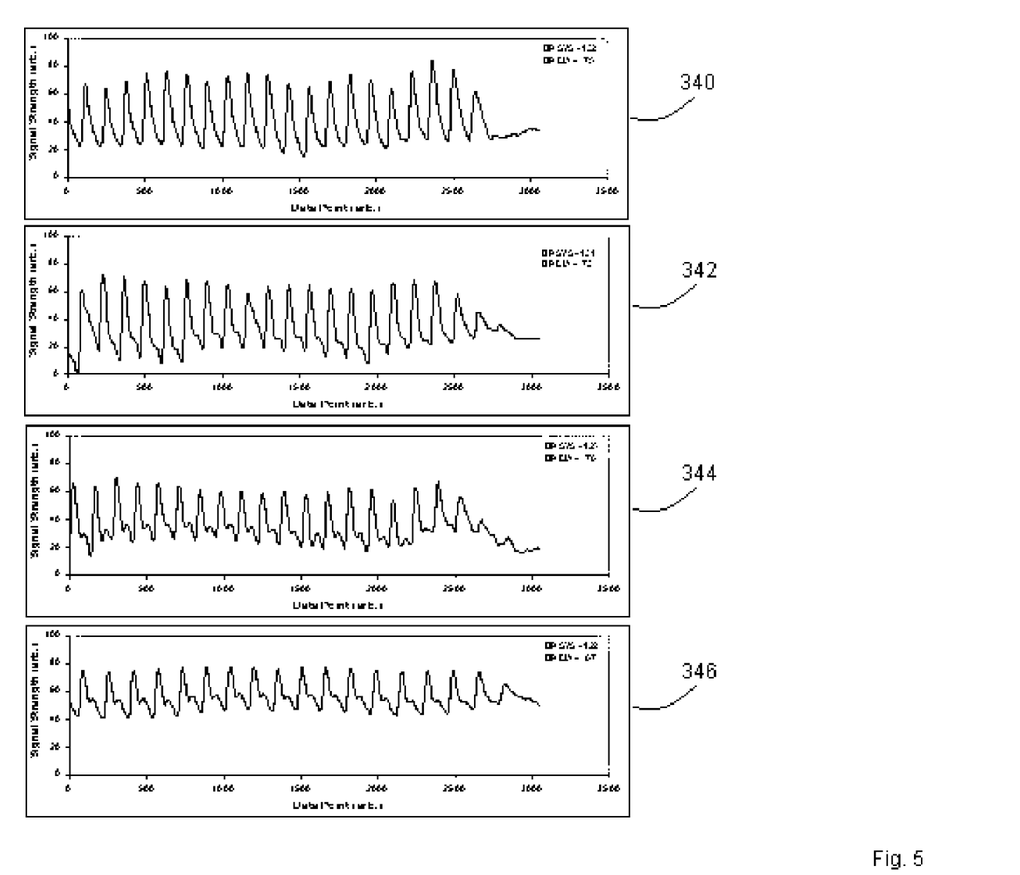
FIG. 5 is an image of four different graphs of optical waveforms for four different blood pressure measurements.

FIG. 5 shows how pulses within the optical waveform vary with blood pressure. The figure includes four optical waveforms 340, 342, 344, 346, each corresponding to a different blood pressure. The first optical waveform 340 corresponds to a blood pressure of 132 mmHg (systolic) and 75 mmHg (diastolic) and features a heart rate of 110 bpm; the secondary peak is absent, and thus the ratio between the secondary and primary peaks is 0. In the second waveform 342, the heart rate decreases to 106 bpm, and blood pressure correspondingly decreases to 131 mmHg (systolic) and 73 mmHg (diastolic). The secondary peak begins to appear in the second waveform 342, resulting in a ratio between the secondary and primary peaks of 0.19. The third 344 and fourth 346 waveforms show that the patient's heart rate decreases and the ratio increases as both systolic and diastolic blood pressure continue to decrease. Table 1, below, describes these relationships in more detail.

TABLE 1 relationship between blood pressure and calibration parameters

| Optical Waveform | Heart Rate (bpm) | Ratio of Secondary/Primary Peaks | Systolic BP (mmHg) | Diastolic BP (mmHg) |
| --- | --- | --- | --- | --- |
| 340 | 110 bpm | 0.0 | 132 | 76 |
| 342 | 106 bpm | 0.19 | 131 | 73 |
| 344 | 103 bpm | 0.30 | 126 | 70 |
| 346 | 89 bpm | 0.34 | 122 | 67 |

Figure 6:
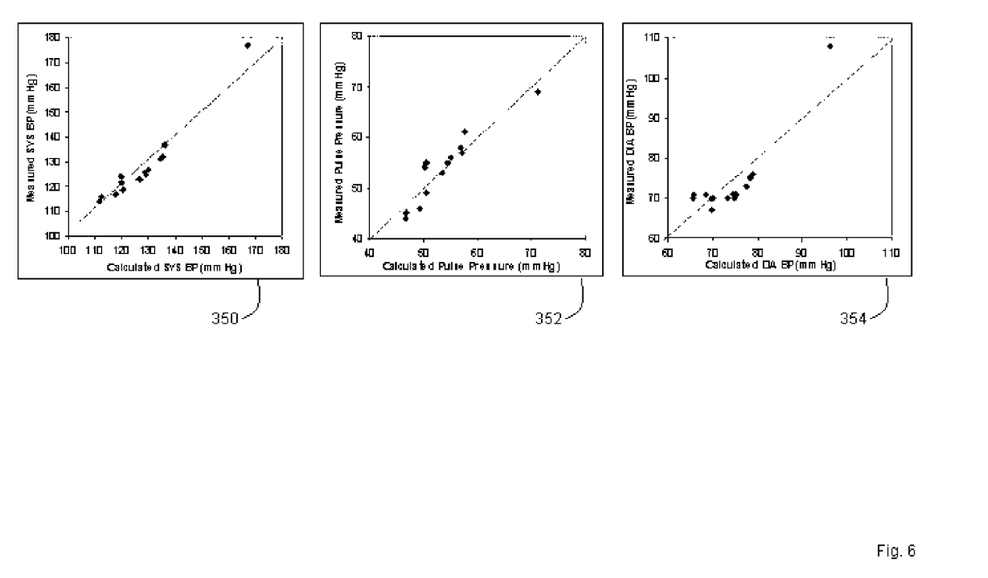
FIG. 6 is an image of three different graphs comparing blood pressure measured with a conventional cuff (y-axis) to blood pressure calculated using a calibration-based approached following a cuffless measurement (x-axis).

FIG. 6 indicates the efficacy of the above-described calibration-based approach to measuring blood pressure. The figure includes graphs 350, 352, 354 that compare blood pressure measured with a conventional cuff (y axis) to blood pressure calculated using a calibration-based approach following a cuffless measurement (x axis). Each graph 350, 352, 354 includes a dashed line indicating perfect, 1:1 correlation. The first graph 350 shows results for systolic blood pressure. Correlation for these measurements is very good, with the average difference between the conventional and cuffless measurements being 3.2 mmHg. The second graph 352 is for pulse blood pressure (the difference between systolic and diastolic blood pressure) and features an average difference between the conventional and cuffless measurements of 1.9 mmHg. The third graph 354 is for diastolic blood pressure and features an average difference between the conventional and cuffless measurements of 3.8 mmHg.

Figure 7:
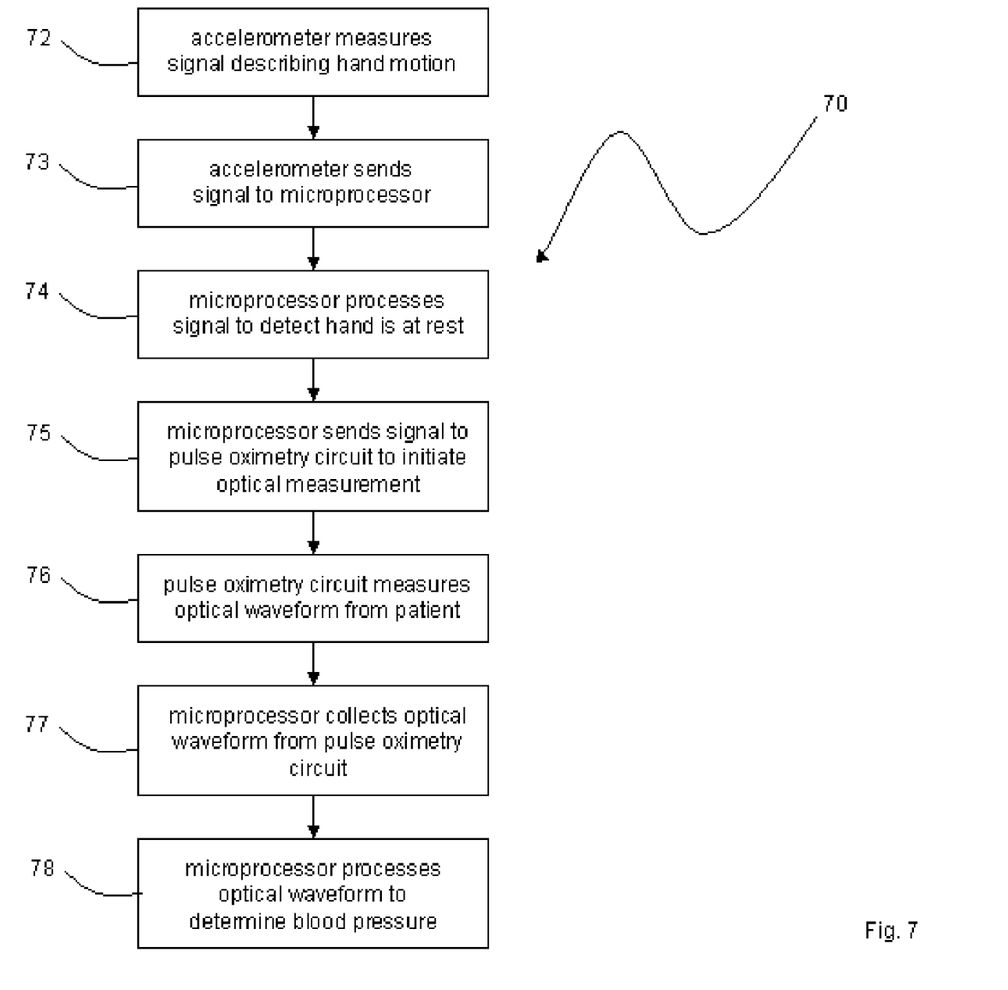
FIG. 7 is a flow chart showing an algorithm that processes signals from an accelerometer within a monitoring device of the present invention to determine an optimal time to make a measurement.

In a preferred embodiment, the data-processing circuit 18 of the monitoring device 10 employs an algorithm that detects a signal from an accelerometer 34 and processes the signal to determine if a user's hand is at rest or in motion. The microprocessor then uses this algorithm to determine the exact time to take a measurement. FIG. 7, for example, shows a preferred method of one such algorithm 70. In the algorithm 70, at block 72, the accelerometer 34 measures signals (e.g. voltage) that vary with motion of the user's hand. At block 73, the accelerometer 34 sends the signals to the microprocessor. At block 74, the microprocessor processes the signals to detect if the hand is at rest or in motion. At block 75, in response to detecting the hand at rest, the microprocessor sends a signal to the pulse-oximetry circuit 35 to initiate the above-described optical measurements. At block 77, the microprocessor then collects an optical waveform from the pulse-oximetry circuit 35. At block 78, the microprocessor processes the optical waveform as described above to determine the vital signs of the patient or athlete.

Figure 8:
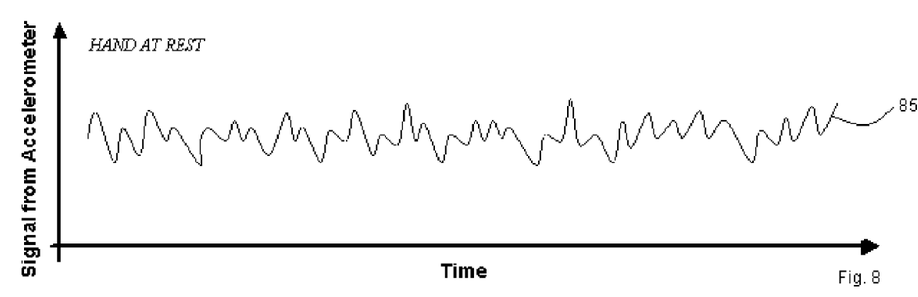
FIG. 8 is a graph depicting a time-dependent signal from an accelerometer within a monitoring device of the present invention when a user's hand is at rest.
Figure 9:
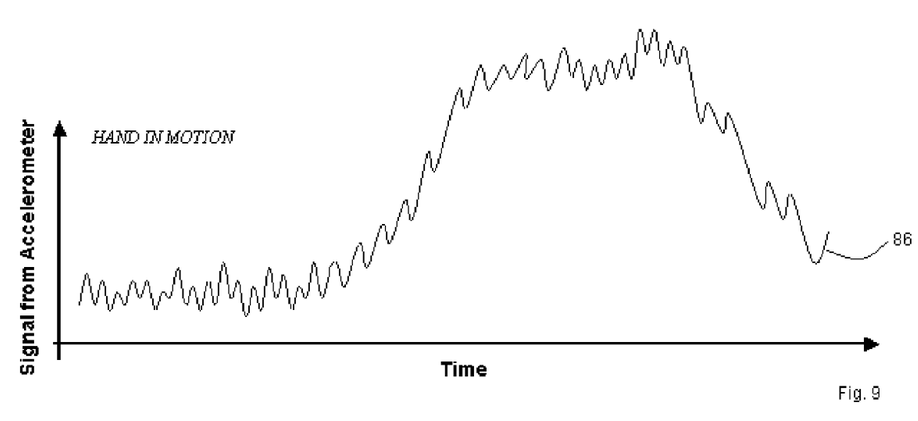
FIG. 9 is a graph depicting a time-dependent signal from an accelerometer within a monitoring device of the present invention when a user's hand is in motion.

FIGS. 8 and 9 are graphs that show how signals from the accelerometer 34 differ when the user's hand is at rest (FIG. 8), i.e. the optimal time to make a measurement, or are in motion (FIG. 9). Referring first to FIG. 8, the time-dependent signal 85 from the accelerometer 34 is basically constant, indicating that the user's hand is at rest. The signal is relatively invariant because the accelerometer 34 does not generate a significant motion-induced variance in signal. FIG. 9 shows a signal 86 that gradually increases and then decreases over time. The increase in signal indicates that the hand is moving in one direction, while the decrease in signal indicates the hand is moving in an opposite direction.

Figure 10:
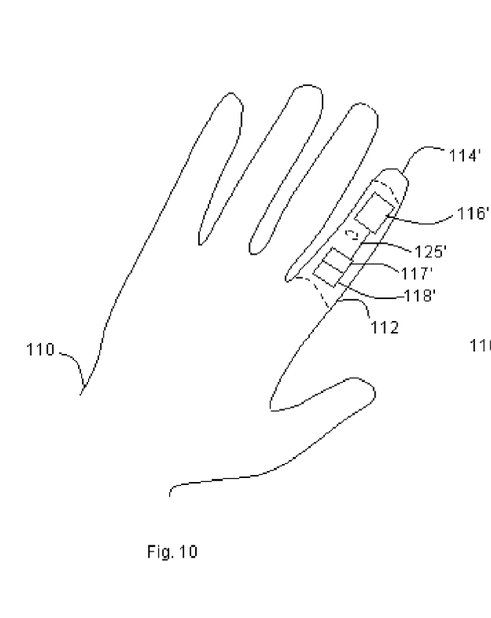
FIG. 10 is a schematic view of an alternative embodiment of the monitoring device of the present invention worn on a user's finger.
Figure 11:
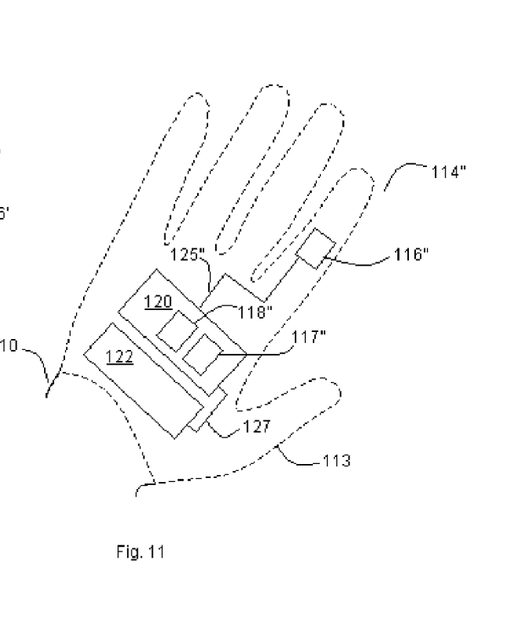
FIG. 11 is a schematic view of an alternative embodiment of the monitoring device of the present invention worn on a user's hand.

In other embodiments of the monitoring device of the present invention, shown in FIGS. 10 and 11, a finger-worn band 112 (FIG. 10) or a hand-worn glove 113 (FIG. 11) supports the accelerometer 117', 117" and vital-sign monitor 116', 116". These components connect to the data-processing circuit 118', 118" through an electrical lead 125', 125". In both cases, the vital-sign monitor 116', 116" includes a small-scale integrated optical system, not shown in the figures but described in detail above, that optically measures blood flow from the athlete's index finger 114', 114" to determine heart rate, pulse oximetry, and blood pressure.

In FIG. 10, for example, the accelerometer 117', vital-sign monitor 116', and data-processing circuit 118' are miniaturized circuit components (e.g., custom made ASICs) supported by a flexible circuit board integrated directly into the finger-worn band 112. In this case, the band 112 is preferably made of a comfortable, non-conductive material, such as neoprene rubber. The glove 113 shown in FIG. 11 features more surface area than the finger-worn band 112 of FIG. 10, and thus the need to reduce the components' size is somewhat relaxed. For example, the glove 113 includes a flexible circuit board 120 that supports the accelerometer 117" and the data-processing circuit board 118". The vital-sign monitor 116", supported by the glove's fabric proximal to the athlete's index finger 114", connects to the data-processing circuit board 118" by the electrical lead 125" that too is integrated in the glove's fabric. In addition, the glove 113 includes a flexible display 122 that connects to the data-processing circuit 118" using another electrical lead 127 to display, e.g., information relating to the athlete's vital signs and motion. The glove 113, for example, could be an exercise glove, such as that used during biking.

In other embodiments, the finger-worn band (FIG. 10) or a hand-worn glove (FIG. 11) can process the above-described optical waveform to measure a user's heart rate during periods of rest or exercise, and then transmit this information to a personal computer using the above-described short-range wireless transmitter. The personal computer can operate a software program that determines how the user's heart rate changes over time.

In other embodiments, placement of the optical, mechanical, and electrical modules described above can be modified to change the form factor of the monitoring device 10. Other configurations of the above-described optical, mechanical, and electrical sensors are also within the scope of the invention. The data-processing circuit 18 can also use algorithms other than those described above to process data measured by the wrist-worn 11 and finger-worn 13 modules. These algorithms are typically based on the equations described above, but may vary in their form. In other embodiments, electrical components within the monitoring device 10 (as shown in FIG. 2) differ from those described above, or are consolidated into a single silicon-based device, such as a custom-made ASIC.

In addition, the monitoring device 10 described above can be used to dynamically track and characterize vital signs along with hand and arm motions in a range of different competitive and training activities, including tennis, boxing, martial arts, racquetball, squash, football, baseball, softball, cricket basketball, soccer, hockey, lacrosse, track and field, various forms of dance and other athletic activities that employ swinging of an arm. In still other embodiments, the monitoring device 10 can be used to characterize general ergonomic activities, including general and repetitive hand and leg movements involved with typing and manipulation of objects.

In still other embodiments, electrical cables shown in FIGS. 1, 10, and 11 can be replaced with a wireless interface, such as a short-range wireless transmitter.

By characterizing both motion and vital signs in real-time, the monitoring device 10 can monitor performance and the physiological performance of athletes participating in actual sporting events. Measurements can be made completely unobtrusive to the athlete without affecting their performance. Trends in the athlete's performance, such as an increase in heart rate, or a sudden drop in pulse oximetry, can be easily determined with the external computer. Algorithms running on this computer can further process this information to monitor additional properties concerning the athlete's effectiveness and health.

The monitoring device described herein is small, easily worn by the athlete during periods of exercise, training, matches, or general day-to-day activities. It makes non-invasive measurements in a matter of seconds with no affect on the athlete. Furthermore, the on-board microprocessor can analyze the time-dependent measurements to generate detailed statistics (e.g., average values, standard deviations, beat-to-beat pressure variations) that are not available with conventional devices that only measure properties at isolated times.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes, modification and substitutions of equivalents may be made therein without departing from the spirit and scope of this invention which is intended to be unlimited by the foregoing except as may appear in the following appended claims. Therefore, the embodiments of the invention in which an exclusive property or privilege is claimed are defined in the following appended claims.

What is claimed is:

1. A device for monitoring a user's blood pressure while the user is ambulatory, the device comprising:
   a blood pressure sensor comprising:
      a motion sensor for monitoring motion of the user and configured to generate motion information in response; and
      a blood pressure monitor comprising an optical system comprising a light source and a light detector configured to generate a time-dependent waveform comprising a primary peak and a reflective peak that are, collectively, representative of the user's blood pressure; and
   a body-worn processing unit, connected to the blood pressure sensor through a cable, comprising:
      a microprocessor for receiving the time-dependent waveform from the blood pressure monitor and motion information from the motion sensor, the microprocessor comprising computer code that controls the microprocessor to: 1) analyze the primary and reflective peaks comprised by the time-dependent waveform from the blood pressure monitor with a mathematical model by varying parameters of the model until they correspond to the amplitudes of the primary and reflective peaks; 2) analyze the motion information from the motion sensor to distinguish between time-dependent waveforms generated while the user is moving and while the user is at rest; and 3) calculate a blood pressure value from parameters of the model determined from the time-dependent waveform generated when the user is at rest.

2. The device according to claim 1 wherein the motion sensor is an accelerometer, a piezoelectric device or a mercury switch.

3. The device according to claim 1 wherein the motion sensor is a software algorithm that analyzes the time-dependent waveform from the blood pressure monitor to determine motion.

4. The device according to claim 3, wherein the software algorithm is computer code operating on the microprocessor.

5. The device according to claim 1 further comprising a wireless transmitter.

6. The device according to claim 5, further comprising a wireless transmitter operating a wireless protocol based on 802.15.1, 802.15.4, part-15, or 802.11.

7. The device according to claim 5 further comprising a component adapted to be mounted on a finger of the user.

8. The device according to claim 1 further comprising an analog-to-digital converter in communication with the motion sensor, the optical system, and the microprocessor.

9. The device according to claim 1 wherein the optical system is in communication with a pulse-oximetry circuit.

10. A device for monitoring a user's blood pressure while the user is ambulatory, the device comprising:
    a blood pressure sensor comprising:
       a motion sensor for monitoring motion of the user and configured to generate motion information in response; and
       a blood pressure monitor comprising an optical system comprising a light source and a light detector configured to generate a time-dependent waveform comprising a primary peak and a reflective peak that are, collectively, representative of the user's blood pressure; and a body-worn processing unit, connected to the blood pressure sensor through a cable, comprising:

a microprocessor for receiving the time-dependent waveform from the blood pressure monitor and motion information from the motion sensor, the microprocessor comprising computer code that controls the microprocessor to: 1) analyze the primary peak and the reflective peak comprised by the time-dependent waveform from the blood pressure monitor by taking a derivative of the waveform; 2) analyzing the derivative of the waveform with a mathematical model by varying parameters of the model until they correspond to the derivatives of the amplitudes of the primary and reflective peaks; 3) analyze the motion information from the motion sensor to distinguish between time-dependent waveforms generated while the user is moving and while the user is at rest; and 4) calculate a blood pressure value from the derivative of the time-dependent waveform and the primary and reflected peaks in the waveform generated when the user is at rest.

11. A device for monitoring a user's blood pressure while the user is ambulatory, the device comprising:

a blood pressure sensor comprising:

a motion sensor for monitoring motion of the user and configured to generate motion information in response; and a blood pressure monitor comprising an optical system comprising a light source and a light detector configured to generate a time-dependent waveform comprising a primary peak and a reflective peak that are, collectively, representative of the user's blood pressure; and a body-worn processing unit, connected to the blood pressure sensor through a cable, comprising:

a microprocessor for receiving the time-dependent waveform from the blood pressure monitor and motion information from the motion sensor, the microprocessor comprising computer code that controls the microprocessor to: 1) analyze the time-dependent waveform from the blood pressure monitor by fitting the primary and reflective peaks comprised by the time-dependent waveform with a mathematical model by varying parameters of the model until they correspond to the amplitudes of the primary and reflective peaks; 2) analyze the motion information from the motion sensor to distinguish between time-dependent waveforms generated while the user is moving and while the user is at rest; and 3) calculate a blood pressure value from parameters determined by fitting the primary and reflective peaks comprised by the time-dependent waveform generated when the user is at rest.

12. A method for monitoring a user's blood pressure while the user is ambulatory, the method comprising:

determining if the user is at rest or in motion using a motion sensor;

generating with an optical system a time-dependent waveform while the user is at rest, the time-dependent waveform comprising a primary peak and a reflective peak that are, collectively, representative of the user's blood pressure, the optical system comprising a light source and light detector;

sending the time-dependent waveform to a microprocessor comprised by a body-worn component for processing;

analyzing the primary peak and a reflective peak within the time-dependent waveform with a mathematical model by varying parameters of the model until they correspond to the amplitudes of the primary and reflective peaks; and calculating a blood pressure value from parameters from the model determined from the time-dependent waveform generated when the user is at rest.

13. The method according to claim 12 wherein determining if the user's hand is at rest comprises analyzing a signal sent from a motion sensor to the microprocessor with an algorithm operating on a microprocessor.

14. The method according to claim 13, wherein the motion sensor is an accelerometer.

15. The method according to claim 13, wherein the motion sensor is a piezoelectric device or a mercury switch.

16. The method according to claim 13, wherein the motion sensor is a software algorithm that analyzes the time-dependent waveform from the optical system to determine motion.

17. The method according to claim 13, further comprising wirelessly transmitting the blood pressure value using a radio-frequency transmitter operating a wireless protocol based on 802.15.1, 802.15.4, part-15 or 802.11.

18. The method according to claim 12, further comprising wirelessly transmitting the blood pressure value using a radio-frequency transmitter.

19. A system for monitoring a user's blood pressure while the user is ambulatory, the system comprising:

a blood pressure sensor comprising:

a motion sensor for monitoring motion of the user and configured to generate motion information in response, and a blood pressure monitor comprising an optical system comprising a light source and a light detector configured to generate a time-dependent waveform comprising a primary peak and a reflective peak that are, collectively, representative of the user's blood pressure, and a body-worn processing unit, connected to the blood pressure sensor through a cable, comprising:

a microprocessor for receiving the time-dependent waveform from the blood pressure monitor and motion information from the motion sensor, the microprocessor comprising computer code that controls the microprocessor to: 1) analyze the primary peak and the reflective peak comprised by the time-dependent waveform from the blood pressure monitor with a mathematical model by varying parameters of the model until they correspond to the amplitudes of the primary and reflective peaks; 2) analyze the motion information from the motion sensor to distinguish between time-dependent waveforms generated while the user is moving and while the user is at rest; and 3) calculate a blood pressure value from parameters from the model determined the time-dependent waveform generated when the user is at rest; and a short-range wireless transmitter for transmitting blood pressure information from the microprocessor to an external receiver.

* * * * *